United States Patent [19]

Smiley et al.

[11] 4,424,030
[45] Jan. 3, 1984

[54] INTEGRATED ORAL MAGNETIC OSTEOGENIC AND ORTHODONTIC APPLIANCES

[75] Inventors: Harry Smiley, White Plains; Abraham Blechman, Tappan, both of N.Y.

[73] Assignee: Medical Magnetics, Inc., Ridgewood, N.J.

[21] Appl. No.: 322,423

[22] Filed: Nov. 18, 1981

Related U.S. Application Data

[63] Continuation of Ser. No. 19,427, Mar. 12, 1979, abandoned.

[51] Int. Cl.³ .................................................. A61C 7/00
[52] U.S. Cl. ..................................... 433/18; 128/419 F
[58] Field of Search ............... 433/18; 128/419 F, 82.1

[56] References Cited

U.S. PATENT DOCUMENTS

| | | | |
|---|---|---|---|
| 3,353,271 | 11/1967 | Blechman | 433/18 |
| 3,646,676 | 3/1972 | Mitchell | 433/189 |
| 3,915,151 | 10/1975 | Kraus | 128/419 F |
| 4,017,973 | 4/1977 | Nelson | 433/18 |
| 4,153,060 | 5/1979 | Korostoff | 428/419 F |

FOREIGN PATENT DOCUMENTS 2341300 9/1977 France ................................ 433/189

Primary Examiner—Robert Peshock
Attorney, Agent, or Firm—Hopgood, Calimafde, Kalil, Blaustein & Judlowe

[57] ABSTRACT

Various types of magnetic or electromagnetic appliances attached intra-orally or extra-orally are used to produce osteogenesis and soft tissue repair in the practice of periodontics and orthodontics. Simultaneously, these innovative magnetic modules generate force fields that produce corrective tooth movement.

10 Claims, 5 Drawing Figures

INTEGRATED ORAL MAGNETIC OSTEOGENIC AND ORTHODONTIC APPLIANCES

BRIEF SUMMARY OF THE INVENTION AND DRAWINGS

This application is a continuation of our copending application Ser. No. 019,427, filed Mar. 12, 1979 and now abandoned.

This invention is a total departure from existing dental devices in that it produces soft tissue repair and osteogenesis in the upper and lower jaws accomplished by affixing permanent magnets, electromagnets or electromagnetic induction coils to the teeth, archwires and other suitable devices which create a regenerative current. The extremely low frequency magnetic field produced by mandibular movement in conjunction with its interaction with adjacent internal electrolytes is a source of this regenerative current. These procedures have application in enhancing therapy in periodontics and orthodontics. This is a new and useful therapeutic modaltiy in that it is totally non-invasive as opposed to the present method of treatment of this common disease by surgical intervention.

Concomitantly, these new devices can be used to produce force fields which will induce orthodontic movement when necessary. This latter object is an improvement over the prior art in that it possesses the following advantages:

1. Totally independent mounting of any type of standard orthodontic appliance in use possessing greater flexibility and eliminating interference.
2. Insures the maximum effect of a continuous force field which has heretofore been an unattainable optimal condition necessary for tooth movement by preventing buccal torquing of the magnetic sleeve module.
3. Bio-compatible sleeve to enclose and protect the magnet.
4. Rectangular orthodontic tube or alternate geometric configurations which will resist buccal torquing of the entire magnetic sleeve module is soldered or otherwise suitably connected to the lingual aspect of the sleeve.
5. Proper preparation of the magnets will induce torquing of one magnet when its attractive pole is brought into contact with another magnet. These magnets mounted in accordance with this principle, in this invention, is used in orthodontic therapy where torquing of the teeth is required.
6. For the first time in orthodontic therapy this invention makes possible the use of a force that increases in value as time progresses, i.e., as the magnetic poles approach each other. Fewer orthodontic adjustments and decreased treatment time are attributed to this unique quality of the force.
7. All other orthodontic force systems when used in an intermaxillary mode demonstrate large vertical force vectors which tend to unseat bands and increase the cant of the occlusal plane. This latter effect leads to relapse of treatment.
8. This invention provides for alternate configurations of the magnets and involves a totally new approach in orthodontics so that it utilizes magnets with fields so oriented that when their attractive poles are not perfectly aligned in contact a sliding or shearing force is produced with a minimal air gap between the poles.
9. The flexibility inherent in this invention is not limited to magnetic materials in current use, but may easily be adapted to materials now unknown which develop the suitable properties required. Further, there are innumerable variations including sizes, amounts, shapes of magnets and the electromagnetic and force fields generated.

These advantages will hereinafter be amplified and become more apparent in the data provided in the construction and operation as more fully subsequently described and claimed, reference being had to the annexed drawings forming a part hereof, wherein like numerals refer to like parts throughout, and in which:

DETAILED DESCRIPTION OF DRAWINGS

Figure 1:
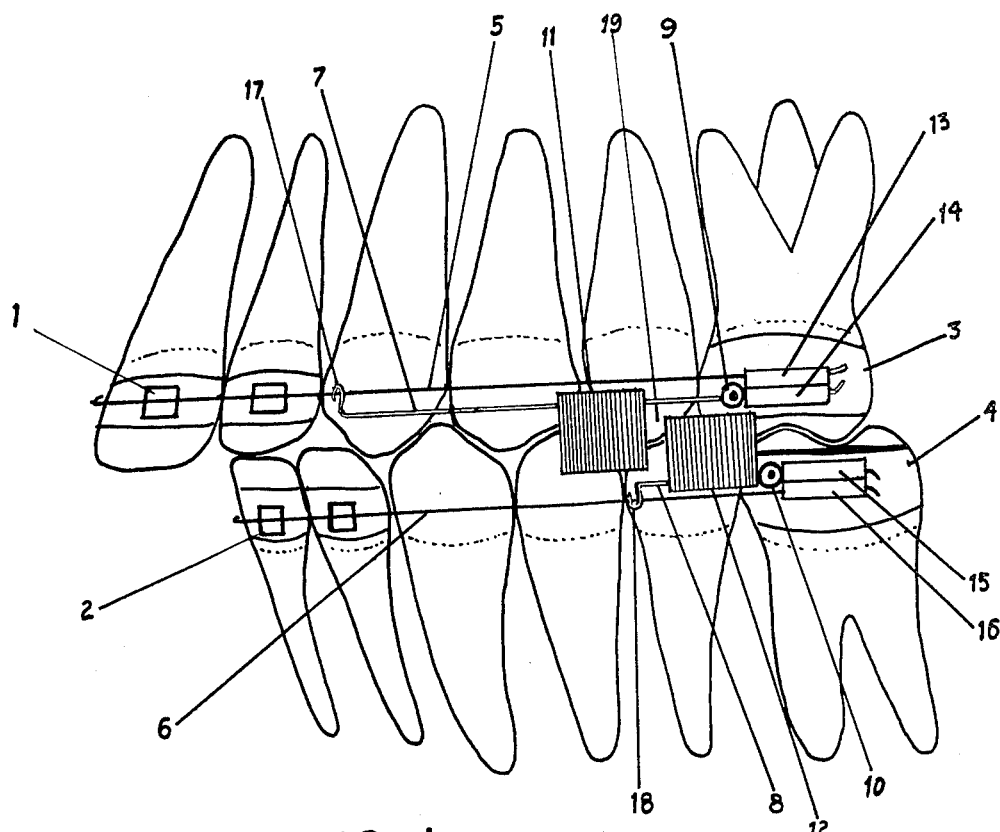
FIG. 1 is a lateral view of an integrated oral magnetic osteogenic and orthodontic appliance mounted on a portion of the dentition of the upper and lower jaw of a human being with a class II malocclusion.

FIG. 1 of the drawings shows an orthdontic appliance mounted on a portion of the dentition of the upper and lower jaw of a human being with a Class II malocclusion. The orthodontic appliance includes upper anterior bands 1 mounted to the anterior teeth and having wire securing brackets thereon, an upper posterior band 3 mounted to an upper rear molar and having a maxillary superior molar tube 13 mounted thereon and an upper archwire 5 connecting the brackets on the anterior bands 1 and the molar tube 13 on the posterior band. The bands and brackets are shown and described in more detail in the Blechman U.S. Pat. No. 3,353,271, issued Nov. 21, 1957. Lower anterior bands 2 with suitable wire mounting brackets thereon are connected by a lower archwire 6 to a mandibular inferior molar tube 16 mounted on a lower molar band 4.

An upper archwire 7 independent of the main archwire 5 is connected at one end to a maxillary inferior molar tube 14 mounted on the molar band 3 and at its other end by a hook extension 17 to the archwire 5. The archwire 7 serves as a support for a magnetic module 11. The magnetic module 11 includes a magnet accommodated within a sleeve. A lock 9 attached to the archwire 7 and intermediate the module 11 and the molar tube 14 permits fore-and-aft adjustment of the magnetic module 11.

A lower archwire 8 independent of the archwire 6 supports a magnetic module 12 thereon. The archwire 8 is connected at one end to a mandibular superior molar tube 15 mounted on the band 4 and at the other end by a hook extension 18 of the archwire 8 to the archwire 6. A lock 10 attached to the lower archwire 8 intermediate the module 12 and the molar tube 15 permits fore-and-aft adjustment of the magnetic module 12.

The magnetic modules 11 and 12 are spaced apart end to end to provide an air gap 19 between the attractive poles of the magnets. This air gap can be adjusted by moving the modules when required to regulate the magnetic force between them. The orientation of the magnetic modules 11 and 12 can also be adjusted relative to each other by bending the archwires 7 and 8 so that the poles of the magnet can be aligned.

The archwires 7 and 8 and the passages through the molar tubes 14 and 15 which anchor the archwires 7 and 8 are preferably of rectangular cross section, for example, 0.022"×0.028" to prevent buccal torquing of the magnetic modules when the archwires 7 and 8 are inserted therein, thereby permitting the poles of the magnetic modules 11 and 12 to remain properly aligned at all times so that continuous orthodontic movement will be accomplished.

The integrated oral magnetic osteogenic and orthodontic appliance shown in FIG. 1 creates a magnetic field in the adjacent bony tissue so that mandibular movement during mastication, speech, etc. generates a low frequency changing electromagnetic field which arises from the minor hysteresis loop in the second quadrant and its interaction with circulating vascular inter-cellular electrolytes. Simultaneous orthodontic movement is imparted to the teeth by the magnetic force field. Normally, during tooth movement, osteoclastic activity of the alveolar bone is induced and subsequently osteogenesis must occur to insure successful orthodontic treatment. This invention accelerates the rate of osteogenesis and also stimulates osteogenesis in areas where this is necessary but may not occur. Tooth movement accelerated by the continuous application of force plus increased osteogenic activity accelerates treatment time. In addition, stimulation of osteogenesis in areas where this should occur but fails to occur prevents subsequent periodontal disease and possible early loss of teeth. Thus, this appliance can be utilized in the treatment of periodontal disease even where orthodontic requirements are not necessary.

Figure 2:
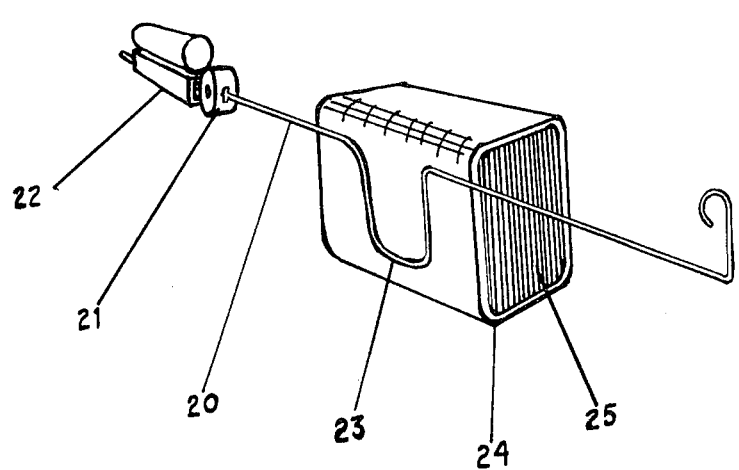
FIG. 2 is a lingual view of reference numerals 11 and 12 in FIG. 1.

FIG. 2 is a more detailed view of one of the magnetic modules 11 or 12 shown in FIG. 1. The magnetic module includes a permanent magnet 25 accommodated within a magnet holding sleeve 24. The sleeve 24, preferably a surgical grade stainless steel, is mounted to an archwire having a hook extension at one end and a buccal tube 22 at the opposite end. The hook extension, as described above in connection with FIG. 1, is adapted to be mounted on another archwire and the buccal tube 22 is adapted to be mounted on a molar band. An orthodontic lock 21 on the archwire 20 prevents the archwire from moving relative to the tube 22 when properly locked in place.

The archwire is of rectangular cross section and is received within a rectangular passage of generally complementary shape in the tube 22. A U-bend 23 in the archwire facilitates attachment of the archwire to the sleeve by soldering, welding or other suitable means.

The permanent magnet is anchored in the sleeve by a bio-compatible adhesive material, such as an acrylic, epoxy, urethane, or other suitable adhesive material. The exposed poles of the magnet are preferably coated with the adhesive material to prevent corrosion products from leaching into the oral cavity when SmCo or AlNiCo magnets are used. When PtCo or other harmless magnetic materials are used, such protective coatings are unnecessary.

Figure 3:
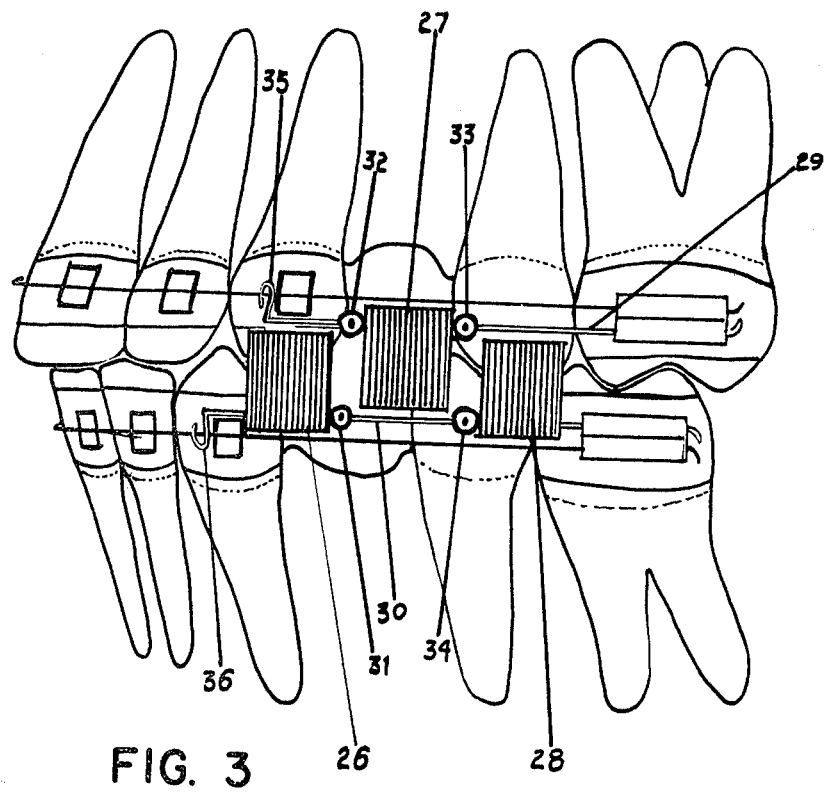
FIG. 3 is a lateral view of a magnetic orthodontic appliance mounted on a portion of the dentition of the upper and lower jaw of a human being with Class I malocclusion requiring extractions.

FIG. 3 of the drawings shows an orthodontic appliance of the present invention mounted on a portion of the upper and lower jaw of a human being with a Class I malocclusion requiring extractions. This appliance utilizes the basic mounting and independent archwires of the appliance described above in connection with FIG. 1.

More specifically, the orthodontic appliance shown in FIG. 3 utilizes three magnetic modules 26, 27 and 28. This middle module 27 is mounted on an upper archwire 29 intermediate a pair of orthodontic locks 32 and 33. The anterior end of the archwire 29 has a hook extension 35 bent to engage the main archwire immediately mesial to a bracket mounted to the upper cuspid to be moved distally. The anterior and posterior magnetic modules 26 and 28, respectively, are mounted to a lower archwire 30, mounted at its posterior end to a lower molar and having a hook extension 36 at its anterior end bent to engage the main archwire immediately mesial to a bracket attached to the lower cuspid to be moved distally. An orthodontic lock 31 is mounted on the archwire 30 distal to the module 26 and an orthodontic lock 34 is mounted on the archwire 30 mesial to the magnetic module 28. The orthodontic locks are provided to lock the modules to the archwires but they can be released to adjust the positions of the modules and the size of the air gaps.

The modules are arranged so that distal movement of the upper and lower cuspid teeth can be accomplished simultaneously. Toward this end, the poles of the magnets are positioned so that the middle module 27 is attracted to the posterior lower module 28 to move the upper cuspid distally. At the same time, the anterior lower module 26 is attracted to the middle module 27 to move the lower cuspid distally. Concomitantly, osteogenesis is induced in the adjacent alevolar bone by mandibular movement.

Figure 4:
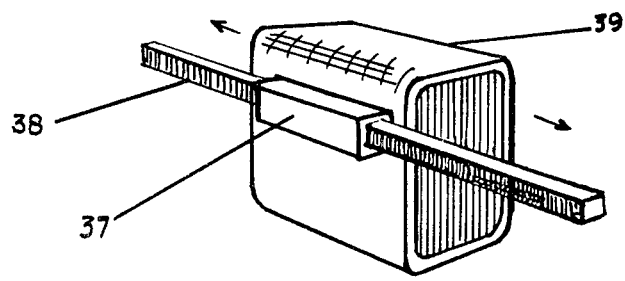
FIG. 4 is a lingual view of reference numerals 26, 27, 28 in FIG. 3.

As shown in FIG. 4 of the drawings, the magnetic module can be provided with a mounting means 37 to facilitate its adjustment on an archwire for adjustment of the air gap between poles of the magnets. The mounting means 37 shown in FIG. 4 is an elongated tube carried by the sleeve 39 to permit the module to be adjusted relative to a supporting archwire 38. The archwire and the passage through the tubular mounting means are of complementary shape, for example, rectangular in cross section, to prevent torquing or twisting of the module on the wire while permitting the module to slide freely along the wire for adjustment.

Figure 5:
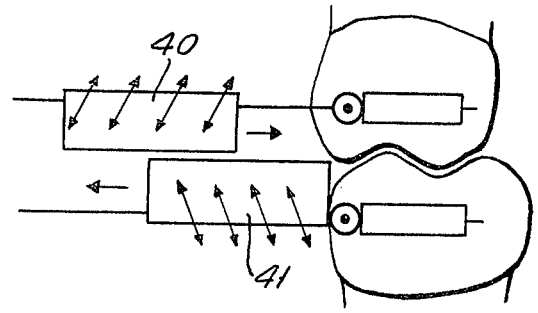
FIG. 5 is a lateral view of a magnetic orthodontic appliance mounted on a portion of the dentition of the upper and lower jaw of a human being demonstrating desirable force fields through shearing with a minimal air gap.

FIG. 5 shows a magnetic orthodontic appliance mounted on a portion of the dentition of the upper and lower jaw of a human being illustrating desirable force fields through shearing with a minimal air gap. A maxillary magnetic module 40 and a mandibular magnetic module 41 are mounted diagonally offset with respect to each other on their respective supporting archwires so that the magnetic fields are oriented diagonally as indicated by the double ended arrows. Since the magnetic poles will tend to align, the shearing effect produces the desired orthodontic forces on the archwires, as indicated by the single ended arrows. The minimal air gap eliminates friction between the poles and simultaneously generates a maximal force. Concomitantly, osteogenesis and soft tissue repair is achieved by the low frequency electromagnetic field described above.

What is claimed is as follows:

1. Dental modules for use in an oral osteogenic and orthodontic appliance in which at least a pair of magnets is adapted to be mounted by archwires to the upper and lower jaws so that the fields will be displaced relative to each other to promote osteogenesis and soft tissue repair, comprising first and second permanent magnets, a non-magnetic and non-corrosive sleeve encasing and protecting each magnet from impact and oxidation and exposing the magnet only at the poles thereof, each such sleeve being of electrically conductive material and being peripherally continuous, whereby flux concentration is enhanced at the poles of each magnet, means fixing the magnet within each sleeve to prevent movement between each magnet and its sleeve, a thin, strong coating on the poles for protecting the magnets from damage due to oxidation and the oral cavity from potentially toxic corrosion products of the magnets, archwire-mounting means on one of the sleeves for mounting the same to the upper jaw, and archwire-mounting means on the other of the sleeves for mounting the same to the lower jaw, said respective mounting means being adapted to position a pole of one magnet in substantially opposed and closely spaced adjacency to a pole of the other magnet at least during a portion of a cycle of jaw articulation; whereby reaction between said magnets develops a tooth-displacement force effective to displace at least one tooth in one of the jaws and to thereby develop a void in the one jaw in the wake of such tooth displacement, and further whereby, in the course of jaw articulation, the magnetic fields of said magnets react to produce in the developing-void region an external field which varies as a function of jaw articulation, said external field being therapeutically beneficial as an aid to formation of new bone in the void region.

2. Dental modules as set forth in claim 1, in which the mounting means for each magnet includes an elongate tube mounted on the associated sleeve for receiving the supporting archwire.

3. Dental modules as set forth in claim 2, including a non-circular passage through the mounting tube of generally complementary shape to the supporting archwire to prevent rotational movement of the involved sleeve relative to the supporting archwire to keep the poles substantially aligned to maximize force.

4. An oral osteogenic and orthodontic appliance in which at least a pair of magnets is adapted to be mounted by archwires to the upper and lower jaws so that magnetic fields will be displaced relative to each other to promote osteogenesis and soft-tissue repair, said appliance including anterior and posterior modules, each module comprising a permanent bar magnet retained within a peripherally continuous shield of electrically conductive material so as to expose the magnet only at its poles, whereby flux concentration is enhanced at the poles of each magnet, main maxillary and mandibular archwires and module supporting maxillary and mandibular archwires offset from the main archwires in a direction toward each other, each module supporting archwire supporting at least one of the modules with one pole of each of the two modules arranged in closely spaced reacting relationship, each module support-archwire being connected at one end to a posterior tooth and supported at the other end by the respective main archwire; whereby reaction between said magnets develops a tooth-displacement force effective to displace at least one tooth in one of the jaws and to thereby develop a void in the one jaw in the wake of such tooth displacement, and further whereby, in the course of jaw articulation, the magnetic fields of said magnets react to produce in the developing-void region an external field which varies as a function of jaw articulation, said external field being therapeutically beneficial as an aid to formation of new bone in the void region.

5. An oral osteogenic and orthodontic appliance as set forth in claim 4, including a third module spaced apart on the same archwire which supports the posterior module so as to accommodate the anterior module supported by the other archwire therebetween.

6. An oral osteogenic and orthodontic appliance in which at least three magnets are adapted to be mounted by archwires to the upper and lower jaws so that magnetic fields will be displaced relative to each other to promote osteogenesis and soft-tissue repair, said appliance including at least three dental modules, each module comprising a permanent bar magnet retained within a peripherally continuous shield of electrically conductive material so as to expose the magnet only at its poles, whereby flux concentration is enhanced at the poles of each magnet, maxillary and mandibular archwires for supporting the dental modules, one module supporting archwire supporting spaced apart anterior and posterior modules and the other supporting an intermediate module, the poles of the intermediate module magnet and adjacent poles of the other module magnets being in substantially opposed and closely spaced adjacency during a portion of a cycle of jaw articulation, and means connecting the anterior end of each archwire to an anterior tooth to apply corrective forces to both maxillary and mandibular anterior teeth.

7. Dental modules for use in an oral osteogenic and orthodontic appliance in which at least a pair of permanent bar magnets is adapted to be mounted by archwires to the upper and lower jaws so that the fields of said magnets will be displaced relative to each other to promote osteogenesis and soft tissue repair, comprising first and second magnets, an elongate sleeve of non-corrosive and electrically conductive material peripherally continuously encasing each magnet and exposing the magnet only at its poles, whereby flux concentration is enhanced at the poles of each magnet, means fixing the magnet within each sleeve to prevent movement between each magnet and its sleeve, a thin, strong coating on the poles for protecting the magnets from damage due to oxidation and the oral cavity from potentially toxic corrosion products of the magnets, archwire-mounting means on one of the sleeves for mounting the same to the upper jaw, and archwire-mounting means on the other of the sleeves for mounting the same to the lower jaw, said respective mounting means being adapted to position a pole of one magnet in substantially opposed and closely spaced adjacency to a pole of the other magnet at least during a portion of a cycle of jaw articulation; whereby reaction between said magnets develops a tooth-displacement force effective to displace at least one tooth in one of the jaws and to thereby develop a void in the one jaw in the wake of such tooth displacement, and further whereby, in the course of jaw articulation, the magnetic fields of said magnets react to produce in the developing-void region an external field which varies as a function of jaw articulation, said external field being therapeutically beneficial as an aid to formation of new bone in the void region.

8. The dental module as set forth in claim 2 or claim 7, in which each sleeve is of stainless steel.

9. The dental module as set forth in claim 2 or claim 7, in which each permanent magnet is of SmCo.

10. Dental modules for use in an oral osteogenic and orthodontic appliance in which at least a pair of permanent bar magnets is adapted to be mounted by archwires to the upper and lower jaws so that the fields of said magnets will be displaced relative to each other to promote osteogenesis and soft tissue repair, comprising first and second such magnets of PtCo, an elongate sleeve of non-corrosive and electrically conductive material peripherally continuously encasing each magnet and exposing the magnet only at its poles, whereby flux concentration is enhanced at the poles of each magnet, means fixing the magnet within each sleeve to prevent movement between each magnet and its sleeve, archwire-mounting means on one of the sleeves for mounting the same to the upper jaw, and archwire-mounting means on the other of the sleeves for mounting the same to the lower jaws, said respective mounting means being adapted to position a pole of one magnet in substantially opposed and closely spaced adjacency to a pole of the other magnet at least during a portion of a cycle of jaw articulation; whereby reaction between said magnets develops a tooth-displacement force effective to displace at least one tooth in one of the jaws and to thereby develop a void in the one jaw in the wake of such tooth displacement, and further whereby, in the source of jaw articulation, the magnetic fields of said magnets react to produce in the developing-void region an external field which varies as a function of jaw articulation, said external field being therapeutically beneficial as an aid to formation of new bone in the void region.

* * * * *